(12) United States Patent
Erskine-Smith

(10) Patent No.: US 9,027,162 B2
(45) Date of Patent: May 12, 2015

(54) EYE WEAR

(76) Inventor: Craig Mathew Erskine-Smith, North Curl Curl (AU)

( * ) Notice: Subject to any disclaimer, the term of this patent is extended or adjusted under 35 U.S.C. 154(b) by 0 days.

(21) Appl. No.: 13/814,411

(22) PCT Filed: Jun. 23, 2011

(86) PCT No.: PCT/AU2011/000774
§ 371 (c)(1),
(2), (4) Date: Mar. 4, 2013

(87) PCT Pub. No.: WO2012/016271
PCT Pub. Date: Feb. 9, 2012

(65) Prior Publication Data
US 2013/0152261 A1    Jun. 20, 2013

(30) Foreign Application Priority Data
Aug. 5, 2010 (AU) ................. 2010903500

(51) Int. Cl.
*A42B 1/00* (2006.01)
*A41D 13/11* (2006.01)
*A61F 9/02* (2006.01)

(52) U.S. Cl.
CPC ............ *A41D 13/1184* (2013.01); *A61F 9/025* (2013.01); *A61F 9/026* (2013.01); *A61F 9/027* (2013.01)

(58) Field of Classification Search
CPC ........................................ A42B 3/20
USPC .......... 2/9, 12, 13, 15, 426, 174, 428; 351/41, 351/69, 87, 104, 136
See application file for complete search history.

(56) References Cited

U.S. PATENT DOCUMENTS

| | | | |
|---|---|---|---|
| 5,302,977 A | 4/1994 | Markovitz | |
| 5,495,303 A * | 2/1996 | Kolentsi | 351/43 |
| 5,940,892 A * | 8/1999 | Morgan | 2/430 |
| 6,532,598 B1 | 3/2003 | Cardarelli | |
| 6,666,554 B2 * | 12/2003 | Mulvey | 351/107 |
| 6,694,532 B2 * | 2/2004 | Chen | 2/428 |
| 7,062,797 B2 | 6/2006 | Khulusi | |
| 8,087,776 B2 * | 1/2012 | Pulito | 351/137 |

FOREIGN PATENT DOCUMENTS

| | | |
|---|---|---|
| CN | 2756187 Y | 8/2006 |
| CN | 201422956 Y | 3/2010 |
| EP | 0 516 169 A1 | 12/1992 |
| WO | 86/00012 | 1/1986 |

OTHER PUBLICATIONS

ISR for PCT/AU2011/000774 mailed on Aug. 18, 2011.
PCT International Preliminary Report on Patentability Chapter I from PCT/AU2011/000774 dated Feb. 5, 2013.
PCT Written Opinion of the International Search Authority from PCT/AU2011/000774 dated Aug. 18, 2011.

* cited by examiner

*Primary Examiner* — Tejash Patel
(74) *Attorney, Agent, or Firm* — Ladas & Parry, LLP

(57) ABSTRACT

Eye wear (10) that may be employed in the health industry. The eye wear (10) includes a shield (11) that is formed of a sheet of flexible material, such as plastic. A seal (19) is secured to a major face of the shield (11) and is formed of a strip of flexible plastics material such as foam, with the seal (19) extending beyond the shield (11) so as to provide the loops (23) that engage a user's ears to aid in securing the eye wear to the user's face.

12 Claims, 4 Drawing Sheets

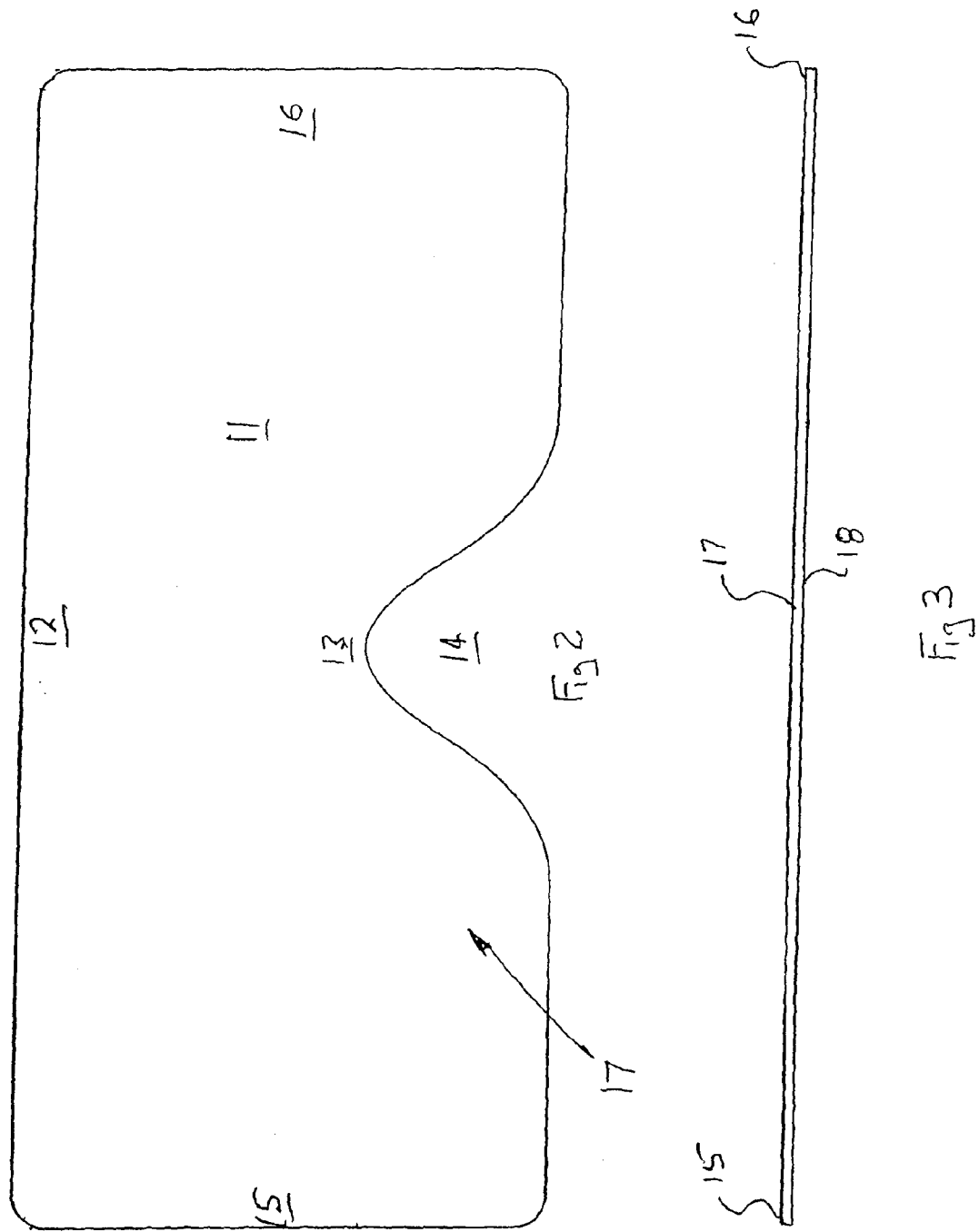

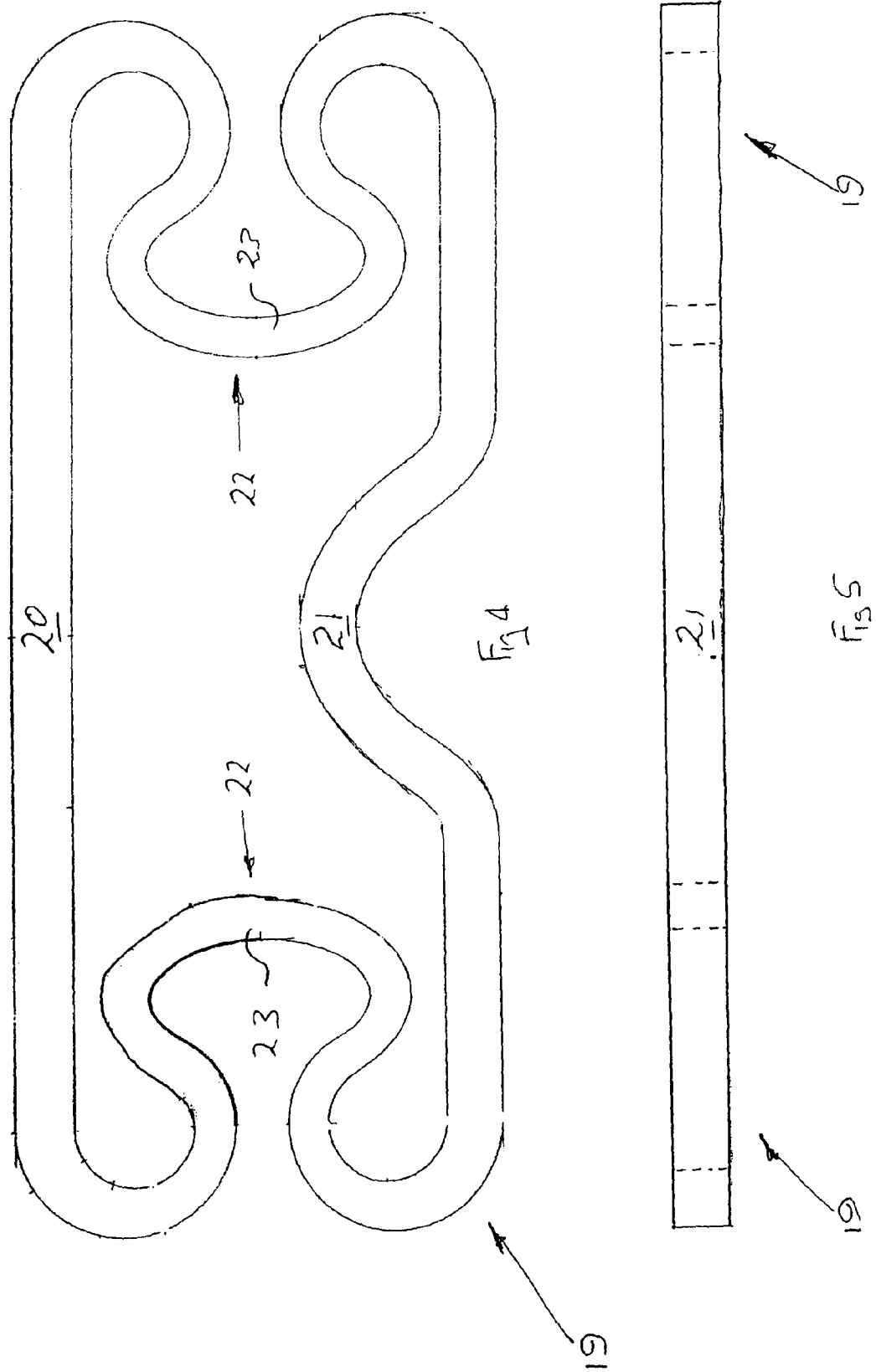

EYE WEAR

CROSS-REFERENCE TO RELATED APPLICATIONS

This application is the U.S. National Stage of International Patent Application No. PCT/AU2011/000774 filed on Jun. 23, 2011, which claims priority to Australian Patent Application No. 2010903500 filed on Aug. 5, 2010, the disclosures of which are hereby incorporated by reference in their entireties.

TECHNICAL FIELD

The present invention relates to eye wear to protect a user's eyes.

BACKGROUND OF THE INVENTION

Eye wear is used in many instances to protect the eyes of a wearer. For example, eye wear is used in industrial purposes where machinery is being operated. Protective eye wear is also employed in the healthcare industry. As particular examples, healthcare professionals and/or patients use protective eye wear where there is a danger of infection.

Protective eye wear for dental use has generally been adapted from protective eye wear designed for persons in the upright position, rather in the supine position. Because of this available protective eye wear has a number of disadvantages in the dental industry including not fully protecting the user's eyes.

It is not uncommon for protective eye wear used in the healthcare industry to be merely a pair of lens glasses or sunglasses. Not only do they suffer from the above disadvantages, but they have the further disadvantages of being relatively expensive and requiring sterilising. A still further disadvantage is that they are frequently uncomfortable to wear.

OBJECT OF THE INVENTION

It is the object of the present invention to overcome or substantially ameliorate at least one of the above disadvantages.

SUMMARY OF THE INVENTION

There is disclosed herein eye wear to be worn adjacent a user's face, the eye wear including:
a shield to extend across the user's face to cover eyes of the user and to extend between the forehead and nose/cheeks of the user, the shield having a first transverse edge portion to be located adjacent the user's forehead, and a second transverse edge portion to be located adjacent the user's nose/cheeks;
a seal including a first seal length to engage the user's forehead and extending along the first portion, and a second seal length to engage the user's nose and cheek and extending along the second portion; and wherein
the seal further provides securing parts to extend beyond the shield to at least aid in securing the shield to the user's face.

Preferably, the shield is formed of a flexible sheet material, the material being transparent, opaque or translucent.

Preferably, the securing parts include a pair of loops that engage ears of the user to secure the shield to the user's face.

In an alternative preferred form, the securing parts provide at least one loop that is to extend around the user's head to secure the shield to the user's face.

In an alternative preferred form, the seal is integrally formed from resilient material.

Preferably, the seal material is foam.

Preferably, the seal material is plastics or rubber (natural or synthetic).

Preferably, said shield extends laterally beyond said first and second lengths.

Preferably, the shield has side edge portions extending between the transverse edge portions, with a gap between the first seal length and the second seal length at each side edge portion so that the eyewear is spaced from the user's face at the side edge portions.

Preferably, said shield is plastically deformed so as to have cheek engaging portions, the cheek engaging portions being spaced on opposite sides of a nose engaging portion and displaced rearwardly relative thereto.

There is further disclosed herein, a method when used to manufacture eye wear, the method including the steps of:
providing a sheet of plastics material;
forming the sheet to provide a shield to extend across the face of a user;
providing at least one strip of resilient material; and
securing the strip to a major face of the shield, with the strip being positionable to extend beyond the shield to engage a user to at least aid in securing the shield to the user's face.

Preferably, forming the shield to include first and second eye portions to cover the user's eyes, and a recess located between eye portions which a user's nose is to extend, with the seal extending transversely across the shield adjacent the upper edge portion and across the lower edge portion, and to extend beyond the shield to aid in securing the shield to the user.

BRIEF DESCRIPTION OF THE DRAWINGS

A preferred form of the present invention will now be described by way of example with reference to the accompanying drawings wherein:
FIG. 2 is a schematic front elevation of a shield employed in the eye wear of FIG. 1;
FIG. 3 is a schematic side elevation of the shield of FIG. 2;
FIG. 4 is a schematic front elevation of a seal employed in the eye wear of FIG. 1;
FIG. 5 is a schematic side elevation of the seal of FIG. 4.

DETAILED DESCRIPTION OF THE PREFERRED EMBODIMENTS

In the accompanying drawings there is schematically depicted an item of eye wear 10. The eye wear 10 may be employed in the health industry, such as in dental surgeries. Typically the eye wear 10 would be worn by a dental patient so as to protect the patient's eyes.

Figure 1:
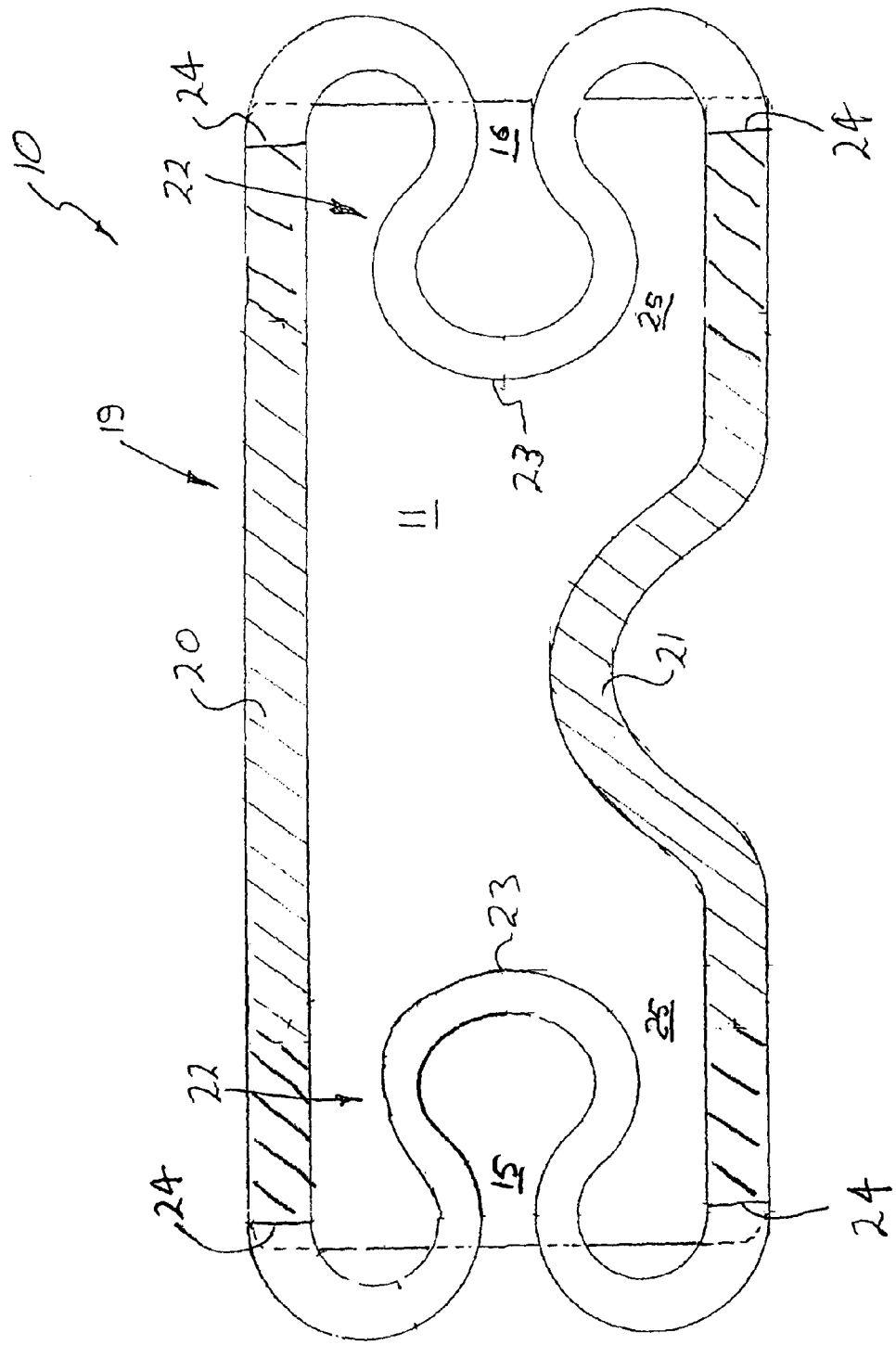
FIG. 1 is a schematic front elevation of an item of protective eye wear.
Figure 6:
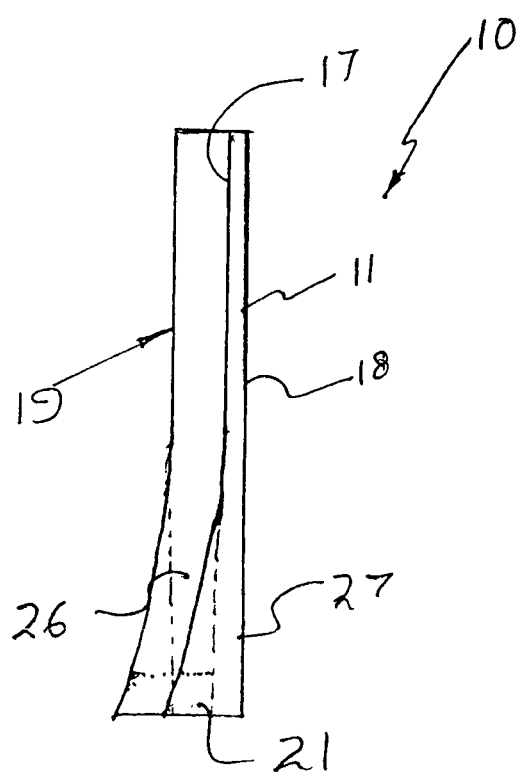
FIG. 6 is a schematic front elevation of a modification of the seal of FIG. 4.

The eye wear 10 includes a shield 11 that is formed of a sheet of flexible material, such as plastics. By being formed of flexible material, the shield 11 can at least partly deform to conform to the contours of the wearer's face. The shield 11 may be transparent, opaque or translucent, or alternatively may be coloured. The shield 11 has a first transverse edge portion 12 that is to be located adjacent the user's forehead, and a second transverse edge portion 13 that is to be located adjacent the user's cheeks and nose. As is best seen in FIGS. 1 and 2, the second portion 13 includes a recess 14 to accommodate a user's nose. Side edge portions 15 and 16 extend between the portions 12 and 13. In this embodiment, the shield 11 is of a generally rectangular configuration, except from the recess 14.

The shield 11 has a first major face 17 that is to be positioned adjacent the user's face, and a second major face 18 that is remote from the user's face.

Secured to the face 17 is a seal 19. The seal 19 is formed of resilient material and more preferably is formed of a foamed resilient material. As a particular example, the material forming the seal 19 may be a foamed plastics material or a foamed rubber (natural or synthetic).

The seal 19 is in the form of a strip that is preferably cut from a sheet or moulded so that it is of a unitary construction. In this embodiment, the seal 19 includes a first length 20 that is to engage the user's forehead. The length 20 is also secured to the face 17 so as to extend longitudinally along the portion 12. The length 20 sealingly connects the shield 11 to the user's forehead.

The seal 19 includes a second length 21 that is to engage the user's nose and adjacent cheek area. The length 21 is secured to the surface 17 so as to extend longitudinally along the portion 13.

The lengths 20 and 21 are secured to the shield 11 at the "hatched" areas as best seen in FIG. 1.

As seen in FIGS. 4 to 8, the seal 19 further includes securing portions 22 that in this embodiment form loops 23 that extend around the user's ears to secure the shield 11 against the user's face covering the user's eyes.

In alternative embodiments, the securing portions 22 may form one or more bands that extend around the user's head so as to again secure the shield 11 in position covering the user's eyes.

Preferably an adhesive would be applied to the surface 17 and/or lengths 20 and 21 so as to cover the "hatched" areas seen in FIG. 1. Accordingly the securing portions 22 would be deflectable from the surface 17 from the adhesive ends 24.

In an alternative embodiment, the lengths 20 and 21 are secured to the surface 17 by ultrasonic welding. In this modification again, fixing of the lengths 20 and 21 to the surface 17 terminates at ends 24. Accordingly, adjacent the side edge portions 15 and 16 there is a gap 25 that exists between the lengths 20 and 21, in particular the ends 24.

Preferably the shield 11 is plastically deformed so as to have cheek engaging portions 26 that are rearwardly spaced on opposite sides of a nose engaging portion 27, that extends angularly over the user's nose, with the cheek engaging portions 26 extending rearwardly therefrom.

The configuration of the eye wear 10 can be modified to suit adults and children as well as males and females.

An advantage of the above described preferred embodiment is that the eye wear 10 can be manufactured at reasonable cost and therefore can be disposed of, overcoming the need for sterilization. A further advantage is that the lengths 20 and 21 sealingly connect the shield 11 with the user's face to inhibit material engaging the user's eyes.

A further advantage of the above described preferred embodiment is that the securing portions 23, by being formed of resilient material, can be elastically deformed and therefore urge the shield 11 toward the user's face.

A still further advantage of the above described preferred embodiment is the gaps 25. The gaps 25 allow for ventilation thereby ameliorating any problems that may exist in relation to condensation of the inside lense. A still further advantage in that regard is that a patient feels less confined, Particularly with respect to the embodiment of FIG. 6, the shield 11 particularly closes the gap between the shield 11 and those areas adjacent the user's cheek and nose.

The invention claimed is:

1. Eye wear to be worn adjacent a user's face, the eye wear including:
   a shield to extend across the user's face to cover eyes of the user and to extend between the forehead and nose/cheeks of the user, the shield having a first transverse edge portion to be located adjacent the user's forehead, and a second transverse edge portion to be located adjacent the user's nose/cheeks;
   a seal including a first seal length to engage the user's forehead and extending along the first portion, and a second seal length to engage the user's nose and cheeks and extending along the second portion; and wherein
   the seal further provides securing parts to extend beyond the shield to at least aid in securing the shield to the user's face.

2. The eye wear of claim 1, wherein the shield is formed of a flexible sheet material, the material being transparent, opaque or translucent.

3. The eye wear of claim 1, wherein, the securing parts include a pair of loops that engage ears of the user to secure the shield to the user's face.

4. The eye wear of claim 1, wherein the securing parts provide at least one loop that is to extend around the user's head to secure the shield to the user's face.

5. The eye wear of claim 1, wherein the seal is integrally formed from resilient material.

6. The eye wear of claim 1, wherein the seal material is foam.

7. The eye wear of claim 1, wherein the seal material is plastics or rubber (natural or synthetic).

8. The eye wear of claim 1, wherein said shield extends laterally beyond said first and second lengths.

9. The eye wear of claim 8, wherein the shield has side edge portions extending between the transverse edge portions, with a gap between the first seal length and the second seal length at each side edge portion so that the eyewear is spaced from the user's face at the side edge portions.

10. The eye wear of claim 1, wherein said shield is plastically deformed so as to have cheek engaging portions, the cheek engaging portions being spaced on opposite sides of a nose engaging portion and displaced rearwardly relative thereto.

11. A method when used to manufacture eye wear, the method including the steps of:
    providing a sheet of plastics material;
    forming the sheet to provide a shield to extend across the face of a user;
    providing at least one seal strip of resilient material to sealingly engage the user's face; and
    securing the strip to a major face of the shield, with the strip being positionable to extend beyond the shield to engage a user to at least aid in securing the shield to the user's face.

12. The method of claim 11, further including the step of forming the shield to include first and second eye portions to cover the user's eyes, and a recess located between eye portions which a user's nose is to extend, with the seal extending transversely across the shield adjacent the upper edge portion and across the lower edge portion, and to extend beyond the shield to aid in securing the shield to the user.

* * * * *